(12) United States Patent
Trevino et al.

(10) Patent No.: US 10,316,312 B2
(45) Date of Patent: *Jun. 11, 2019

(54) COMPOSITION AND METHOD FOR DELIVERY OF MICROORGANISMS IN A DRY MODE IN POROUS STRUCTURE

(75) Inventors: Ramiro Trevino, McKinney, TX (US); Steven R. Ellis, McKinney, TX (US)

(73) Assignee: DRYLET, LLC, Prosper, TX (US)

( * ) Notice: Subject to any disclaimer, the term of this patent is extended or adjusted under 35 U.S.C. 154(b) by 1497 days.

This patent is subject to a terminal disclaimer.

(21) Appl. No.: 13/253,415

(22) Filed: Oct. 5, 2011

(65) Prior Publication Data

US 2012/0083412 A1 Apr. 5, 2012
US 2015/0125923 A9 May 7, 2015

Related U.S. Application Data

(63) Continuation-in-part of application No. 12/898,435, filed on Oct. 5, 2010, now Pat. No. 8,409,822.

(60) Provisional application No. 61/390,029, filed on Oct. 5, 2010, provisional application No. 61/267,520, filed on Dec. 8, 2009, provisional application No. 61/248,724, filed on Oct. 5, 2009, provisional application No. 61/248,776, filed on Oct. 5, 2009.

(51) Int. Cl.
| | |
|---|---|
| C12Q 1/24 | (2006.01) |
| C12N 11/04 | (2006.01) |
| A01N 25/26 | (2006.01) |
| A01N 63/00 | (2006.01) |
| B09C 1/00 | (2006.01) |
| B09C 1/10 | (2006.01) |
| C11B 9/00 | (2006.01) |
| A01N 25/34 | (2006.01) |
| C05B 7/00 | (2006.01) |
| C05B 17/00 | (2006.01) |
| C05C 9/00 | (2006.01) |
| C05D 1/00 | (2006.01) |
| C05D 9/02 | (2006.01) |
| C05F 11/08 | (2006.01) |
| A23P 10/30 | (2016.01) |
| A23L 29/00 | (2016.01) |
| A23L 27/00 | (2016.01) |
| A23L 33/10 | (2016.01) |
| A23L 33/105 | (2016.01) |
| A23L 33/115 | (2016.01) |
| A23L 33/135 | (2016.01) |
| A23L 33/14 | (2016.01) |
| A23L 33/16 | (2016.01) |

(52) U.S. Cl.
CPC .............. *C12N 11/04* (2013.01); *A01N 25/26* (2013.01); *A01N 25/34* (2013.01); *A01N 63/00* (2013.01); *A23L 27/70* (2016.08); *A23L 27/77* (2016.08); *A23L 29/06* (2016.08); *A23L 29/065* (2016.08); *A23L 33/10* (2016.08); *A23L 33/105* (2016.08); *A23L 33/115* (2016.08); *A23L 33/135* (2016.08); *A23L 33/14* (2016.08); *A23L 33/16* (2016.08); *A23P 10/30* (2016.08); *B09C 1/002* (2013.01); *B09C 1/10* (2013.01); *C05B 7/00* (2013.01); *C05B 17/00* (2013.01); *C05C 9/00* (2013.01); *C05D 1/00* (2013.01); *C05D 9/02* (2013.01); *C05F 11/08* (2013.01); *C11B 9/00* (2013.01)

(58) Field of Classification Search
USPC ........................................................ 435/30
See application file for complete search history.

(56) References Cited

U.S. PATENT DOCUMENTS

| | | | |
|---|---|---|---|
| 3,644,215 A | 2/1972 | Muller | |
| 3,719,496 A | 3/1973 | Chen et al. | |
| 3,726,693 A | 4/1973 | Harris et al. | |
| 3,871,957 A | 3/1975 | Mohan et al. | |
| 3,882,253 A | 5/1975 | Schafer et al. | |
| 4,304,857 A | 12/1981 | Brouillard et al. | |
| 4,434,231 A * | 2/1984 | Jung ............... | C05F 11/08 435/178 |
| 4,591,455 A | 5/1986 | Macedo et al. | |
| 4,647,464 A | 3/1987 | Todd, Jr. et al. | |
| 4,717,561 A | 1/1988 | Krivak et al. | |

(Continued)

FOREIGN PATENT DOCUMENTS

| | | |
|---|---|---|
| CN | 106146076 A | 11/2016 |
| EP | 0 067 459 A1 | 12/1982 |

(Continued)

OTHER PUBLICATIONS

International Search Report and Written Opinion (PCT/US2011/054891), dated Oct. 25, 2012.

(Continued)

*Primary Examiner* — Ralph J Gitomer
(74) *Attorney, Agent, or Firm* — Wilson Sonsini Goodrich & Rosati (57) ABSTRACT

The present invention generally relates to compositions and methods of delivering substances in a dry mode, wherein the compositions include an inert carrier substrate having a porous structure, microorganisms loaded throughout the pores of the inert carrier substrate, and a surface layer disposed on the outer surface of the inert carrier substrate, wherein the surface layer is permeable to molecules that aid in cell growth of the microorganisms such that the composition is operable to allow for increased propagation of the microorganisms within the pores of the inert carrier substrate as compared to another composition having an absence of the surface layer.

34 Claims, 1 Drawing Sheet

(56) References Cited

U.S. PATENT DOCUMENTS

| | | | |
|---|---|---|---|
| 4,746,513 A * | 5/1988 | Smith | 424/408 |
| 4,971,820 A | 11/1990 | Likuski et al. | |
| 5,035,804 A | 7/1991 | Stowe | |
| 5,151,363 A * | 9/1992 | Payne | A01N 37/46 424/93.2 |
| 5,194,279 A | 3/1993 | Okel | |
| 5,395,808 A | 3/1995 | Miller et al. | |
| 5,403,799 A | 4/1995 | Miller et al. | |
| 5,443,845 A | 8/1995 | Felix | |
| 5,552,176 A | 9/1996 | Marino | |
| 5,569,634 A | 10/1996 | Miller et al. | |
| 5,635,214 A | 6/1997 | Ponchon et al. | |
| 5,678,238 A | 10/1997 | Billings et al. | |
| 5,906,843 A | 5/1999 | Dew et al. | |
| 6,001,322 A | 12/1999 | Chevallier et al. | |
| 6,039,874 A | 3/2000 | Teran et al. | |
| 6,184,408 B1 | 2/2001 | Burns et al. | |
| 6,200,475 B1 | 3/2001 | Chen | |
| 6,838,004 B1 * | 1/2005 | Yang et al. | 210/660 |
| 6,991,802 B1 | 1/2006 | Ahola et al. | |
| 7,067,062 B2 | 6/2006 | Yang et al. | |
| 7,153,521 B2 | 12/2006 | Viot | |
| 7,538,067 B2 | 5/2009 | Hu et al. | |
| 8,409,822 B2 | 4/2013 | Trevino et al. | |
| 8,557,234 B1 | 10/2013 | Davis et al. | |
| 9,296,989 B2 | 3/2016 | Trevino et al. | |
| 2003/0026845 A1 | 2/2003 | Etzel et al. | |
| 2003/0091641 A1 | 5/2003 | Tiller et al. | |
| 2004/0146444 A1 * | 7/2004 | Dokter | A01K 1/0152 423/335 |
| 2005/0014237 A1 * | 1/2005 | Lee | 435/123 |
| 2005/0145552 A1 | 7/2005 | Sheets et al. | |
| 2005/0266069 A1 * | 12/2005 | Simmons | A61K 9/1617 424/451 |
| 2006/0019016 A1 | 1/2006 | Torcatis | |
| 2006/0147546 A1 | 7/2006 | Ferlin et al. | |
| 2007/0017195 A1 | 1/2007 | Withiam et al. | |
| 2007/0042184 A1 * | 2/2007 | Coyne | A21D 2/00 428/402.2 |
| 2007/0281063 A1 | 12/2007 | Carapelli | |
| 2008/0071129 A1 | 3/2008 | Yang et al. | |
| 2009/0114569 A1 | 5/2009 | Osaheni et al. | |
| 2009/0120872 A1 | 5/2009 | Kroh | |
| 2009/0211453 A1 | 8/2009 | Nassivera et al. | |
| 2009/0214701 A1 | 8/2009 | Forchhammer et al. | |
| 2009/0232950 A1 | 9/2009 | Brothers, Jr. et al. | |
| 2011/0117068 A1 | 5/2011 | Lang et al. | |
| 2014/0352376 A1 | 12/2014 | Carpenter | |
| 2016/0194603 A1 | 7/2016 | Trevino et al. | |

FOREIGN PATENT DOCUMENTS

| | | |
|---|---|---|
| EP | 1 048 697 A2 | 11/2000 |
| FR | 2 573 772 A1 | 5/1986 |
| GB | 886533 | 1/1962 |
| GB | 938381 | 10/1963 |
| GB | 1253271 | 11/1971 |
| GB | 1262838 | 2/1972 |
| GB | 1412590 A | 11/1975 |
| RU | 2378060 C2 | 1/2010 |
| WO | 1997012965 A1 | 4/1997 |
| WO | 9812491 A1 | 3/1998 |
| WO | 2007139264 A1 | 6/2007 |
| WO | 2008061363 A1 | 5/2008 |
| WO | 2008121078 A1 | 10/2008 |
| WO | WO-2008147296 A1 | 12/2008 |
| WO | WO 2010/054439 * | 5/2010 |
| WO | 2010/108211 A1 | 9/2010 |
| WO | 2010122545 A1 | 10/2010 |
| WO | WO-2018009715 A1 | 1/2018 |
| WO | WO-2018160567 A1 | 9/2018 |

OTHER PUBLICATIONS

Durham et al. Characterization of Inorganic Biocarriers That Moderate System Upsets during Fixed-Film Biotreatment Processes. Appl Environ Microbiol 60(9):3329-3335 (1994).

Durham et al. New composite biocarriers engineered to contain adsorptive and ion-exchange properties improve immobilized-cell bioreactor process dependability. Appl Environ Microbiol 60(11):4178-4181 (1994).

Heitkamp et al. Evaluation of five biocarriers as supports for immobilized bacteria: Comparative performance during high chemical loading, acid shocking, drying and heat shocking. Environmental Toxicology and Chemistry 12(6):1013-1023 (1993).

Kim et al. Evaluation of Bacillus amyloliquefaciens as manure additive for control of odorous gas emissions from pig slurry. African Journal of Microbiology Research 8(26):2540-2546 (2014).

Necasek et al. Drought tolerance of Rhizobium leguminosarum andR. meliloti. Folia Microbiologica 38(4):320-324 (1993).

PCT/US2017/040974 International Search Report and Written Opinion dated Oct. 18, 2017.

PCT/US2018/019961 Invitation to Pay Additional Fees dated Apr. 9, 2018.

U.S. Appl. No. 15/066,956 Office Action dated Nov. 2, 2017.

Montalvo et al. Application of natural zeolites in anaerobic digestion processes: A review. Applied Clay Science 58:125-133 (2012).

PCT/US2018/019961 International Search Report and Written Opinion dated Jul. 16, 2018.

* cited by examiner

COMPOSITION AND METHOD FOR DELIVERY OF MICROORGANISMS IN A DRY MODE IN POROUS STRUCTURE

RELATED APPLICATIONS

This patent application claims priority to U.S. Provisional Patent Application Ser. No. 61/390,029 filed on Oct. 5, 2010 and U.S. Pub. No. 2011/0082040, filed on Oct. 5, 2010, which also claims priority to 61/248,724 filed on Oct. 5, 2009, 61/248,776 filed on Oct. 5, 2009, and 61/267,520 filed on Dec. 8, 2009, all of which are incorporated by reference in their entireties.

BACKGROUND OF THE INVENTION

Field of the Invention

The present invention generally relates to compositions and methods of delivering substances in a dry mode. More specifically, the present invention relates to compositions and methods of delivering substances in a dry mode having a surface layer.

Description of the Related Art

It is very difficult to deliver various substances in a dry form. For example, many essential minerals used to grow food crops exhibit hygroscopic properties when in their dry form. This makes it difficult to handle and store these minerals in dry form as they tend to absorb water moisture from the atmosphere, resulting in a wet, sticky mess that does not flow easily. Hygroscopic minerals are usually prilled and coated or are crystallized to limit their natural hygroscopic properties. While this keeps the solids in a usable and flowable form, it limits their ability to dissolve in other liquids for final application. If these same minerals are dissolved in water prior to milling, however, transporting and handling of the liquefied version of the minerals creates problems and drastically increases the costs associated with shipping and handling. It would be advantageous to provide compositions and methods for delivery of hygroscopic substances in a dry, flowable form that is readily dissolved or dispersed in water and applied to crops or other applications.

Cellular organisms, such as enzymes, bacteria, and other microorganisms, are typically not sustainable in a dry state. Therefore, these organisms usually must be kept in wet conditions, which, as noted above, create certain hardships related to their shipping and handling. It would be advantageous to provide, compositions and methods for delivery of cellular organisms in a dry form.

Some substances in their liquid states are relatively unstable. For example, substances which are volatile, or substances which contain one or more hydroxyl groups must be used quickly since these unstable liquid substances can lose their efficacy after a few weeks. Therefore, it would be advantageous to provide compositions and methods for delivery of volatile or unstable fluids in a stable state that is shipped in a dry form.

SUMMARY OF THE INVENTION

The present invention is directed to compositions and methods that satisfy at least one of these needs. The present invention relates to compositions having a surface layer and methods of delivering a substance as part of a composition in a dry mode. As used herein, delivering can also include transporting, shipping, and the like. In one embodiment, the substance can be bacteria, enzymes, other microorganisms, or combinations thereof. In another embodiment, the substance can be a liquid additive that can be either organic or inorganic. As used herein with regards to liquid additives, "organic" means substances related to, derived from, or having properties or characteristic of living things. As used herein with regards to liquid additives, "inorganic" means substances composed of minerals rather than having properties or characteristic of living things. Exemplary liquid additives include liquid food, liquid food additives, liquid biotech agricultural ingredients, conventional liquid agricultural ingredients, liquid human wellness and dietary supplements, and liquid fragrances and beauty products.

One embodiment of the invention is a composition for delivering microorganisms in a dry mode that contains an inert carrier substrate having a porous structure, microorganisms loaded throughout the pores of the inert carrier substrate, and a surface layer disposed on the outer surface of the inert carrier substrate. In one embodiment, the surface layer can be selectively permeable, such that the surface layer allows for movement of certain molecules, which aid in sustaining cell growth of the microorganisms loaded throughout the inert carrier substrate. In one embodiment, the surface layer can be permeable to oxygen and carbon dioxide, such that the composition is operable to allow for increased propagation of the microorganisms within the pores of the inert carrier substrate as compared to another composition having an absence of the surface layer. As used herein, propagation refers to the ability of a substance to reproduce. In one embodiment, the surface layer is operable to allow for oxygen exchange, nutrient exchange, respiration, carbon dioxide production and digestion, and enzyme production.

In one embodiment, the inert carrier substrate is selected from the group consisting of diatomaceous earth, walnut and pecan shells, rice hulls, cellulosic clay, montmorillonite clay, bentonite clay, wool, cotton, cellulose, corn cobs, cellulose shells, precipitated silica, and combinations thereof. In one embodiment, the inert carrier substrate can be precipitated silica.

In one embodiment, the surface layer can include an organic phase. Organic phase as used herein with respect to the surface layer means a phase that includes any member of a large class of chemical compounds whose molecules contain carbon. In one embodiment, the organic phase can be lipids, polysaccharides, fatty acids, or combinations thereof. In one embodiment, the fatty acids have between 12 and 20 carbon atoms. In another embodiment, the fatty acids have between 15 and 17 carbon atoms. In one embodiment, the organic phase can include nonionic plant-based surfactants. Preferable pant-based surfactants include, without limitation, polysorbate 20 and polysorbate 80. In one embodiment, the organic phase can include fatty acid alcohols, fatty acids, lipids, lecithin, or combinations thereof. In one embodiment, the fatty acid alcohols have between 12 and 20 carbon atoms. In one embodiment, the fatty acid alcohols can include cetearyl alcohol, cetyl ester, or combinations thereof. In one embodiment, the fatty acid can be saturated, unsaturated, or a combination thereof. Exemplary saturated fatty acids, without limitation, include: palmitic acid, steric acid, arachidic acid, behenic acid, myristic acid, lignoceric acid, or combinations thereof. Exemplary unsaturated fatty acids, without limitation, include: oleic acid, palmitoleic acid, linoleic acid, linolenic acid, Omega-3, Omega-6, or combinations thereof. In one embodiment, possible sources of the fatty acids can include coconut oils, palm oils, vegetable oils, fish oils, or combinations thereof.

In one embodiment, the organic phase can be formed when an emulsion is mixed with the inert carrier substrate.

Furthermore, the emulsion can be formed by mixing a combination of ingredients, wherein the ingredients are selected from the group consisting of lipids, polysaccharides, fatty acids, lecithin plant-based surfactants, emulsifiers, and combinations thereof.

In another embodiment, the surface layer is substantially impermeable to fresh water. In another embodiment, the surface layer is substantially impermeable to deionized water. In one embodiment, the surface layer can be permeated by surfactants, oil, organic solvents, salt water, damp soil, or combinations thereof. In another embodiment, the surface layer is at least partially soluble to surfactants, oil, organic solvents, salt water, damp soil, or combinations thereof. In another embodiment, the surface layer can further include an absence of a protein.

In another embodiment, the surface layer can include squalene, squalane, C40 isoprenoids, phosphatidylglycerol, diphosphatidylglycerol, cardiolipin, phosphatidylethanolamine, monoglycerol phosphate, or combinations thereof.

In one embodiment, the surface layer can include similar components as those contained in bacteria (prokaryotes) and fungi (eukarotes) cell walls. In one embodiment, the surface layer can function in a similar fashion as a cell wall, such that the surface layer is operable to support microbial life and propagation.

In another embodiment, the composition for delivering microorganisms in a dry mode can be practiced without zeolites, aluminosilicates, mineral powder, and/or an acidic polymer. In one embodiment, the composition is operable to breakdown hydrocarbon deposits in water or soil when applied in a dry state. In another embodiment, the composition can also include nutrients loaded in the inert carrier substrate, such that the nutrients are in contact with the microorganisms, wherein the nutrients are operable to provide a food source to the microorganisms loaded throughout the pores of the inert carrier substrate to enhance propagation of the microorganisms.

In another embodiment, the pores of the precipitated silica define a distribution of pore sizes, where a substantial amount of pores have diameters within the range of 38 to 240 nanometers. In another embodiment, the microorganism can be bacteria, enzymes, fungi, archaea, viruses, algae, plankton, *planaria*, protists, or combinations thereof. In another embodiment, the microorganism can be *bacillus* and/or an enzyme. In another embodiment, the composition also includes nutrients loaded throughout the pores of the inert carrier substrate. In another embodiment, the nutrients can be ammonia, nitrogen, ammonium nitrogen, urea, dextrose, dextrin, sugars, proteins, or combinations thereof. In another embodiment, the composition has an initial microorganism count, and the composition is operable to maintain approximately 50 to 400% of the initial microorganism count for a period of time, preferably at least 45 days.

In another embodiment, a composition for delivering volatile fluids in a dry mode contains an inert carrier substrate having a porous structure, a surface layer disposed on the outer surface of the inert carrier substrate, wherein the surface layer is permeable to oxygen and carbon dioxide, and volatile fluids loaded throughout the pores of the inert carrier substrate, the composition having 25 to 75% volatile fluid concentration by weight, the composition operable to maintain approximately 50 to 100% of volatile fluid concentration for a period of time, preferably at least 45 days, more preferably at least 90 days, wherein the volatile fluid has a vapor pressure of at least 0.03 atm at 25° Celsius. As used herein, the term "fluid" is to be understood to include liquids, plasmas, and gases. In another embodiment, the volatile fluid has a vapor pressure of at least 0.08 atm at 25° Celsius. Exemplary volatile liquids include, without limitation, alcohols, gasoline, diesel fuel.

Another embodiment is a composition for delivering essential oils in a dry mode that contains an inert carrier substrate having a porous structure, a surface layer disposed on the outer surface of the inert carrier substrate, wherein the surface layer is permeable to oxygen and carbon dioxide, and an essential oil loaded throughout the pores of the inert carrier substrate, the composition having 25 to 75% essential oil concentration by weight, the composition operable to maintain approximately 50 to 100% of the essential oil concentration for a period of at least 45 days. Exemplary essential oils include, but are not limited to, agar oil, ajwain oil, angelica root oil, anise oil, asafetida, balsam oil, basil oil, bay oil, bergamot oil, black pepper, buchu oil, birch, camphor, cannabis flower, caraway oil, cardamom seed oil, carrot seed oil, cedarwood oil, chamomile oil, calamus root, cinnamon oil, *cistus*, citronella oil, clary sage, clove leaf oil, coffee, clove leaf oil, coriander, costmary oil, costus root, cranberry seed oil, cubeb, cumin oil, cypress, cypriol, curry leaf, davana oil, dill oil, elecampane, eucalyptus oil, fennel seed oil, fir, frankincense oil, galangal, galbanum, geranium oil, ginger oil, goldenrod, grapefruit oil, henna oil, helichrysum, horseradish oil, hyssop, Idaho tansy, jasmine oil, juniper berry oil, lavender oil, *laurus nobilis, ledum*, lemon oil, lemongrass, lime, *litsea cubeba* oil, mandarin, marjoram, melaleuca, Melissa oil (lemon balm), menthe arvensis, mountain savory, mugwort oil, mustard oil, myrrh oil, myrtle, neem tree oil, neroli, nutmeg, orange oil, oregano oil, orris oil, palo santo, parsley oil, patchouli oil, perilla essential oil, pennyroyal oil, peppermint oil, petitgrain, pine oil, ravensara, red cedar, roman chamomile, rose oil, rosehip oil, rosemary oil, rosewood oil, sage oil, sandalwood oil, sassafras oil, savory oil, schisandra oil, spearmint oil, spikenard, spruce, star anise oil, tangerine, tarragon oil, tea tree oil, thyme oil, tsuga, turmeric, valerian, vetiver oil, western red cedar, wintergreen, yarrow oil, ylang-ylang, zedoary, or combinations thereof.

In another embodiment, a composition for delivering a hygroscopic compound in a dry mode that maintains flow contains an inert carrier substrate having a porous structure, a surface layer disposed on the outer surface of the inert carrier substrate, wherein the surface layer is permeable to oxygen and carbon dioxide, and the hygroscopic compound is loaded throughout the pores of the inert carrier substrate, the composition having 25 to 75% hygroscopic compound concentration by weight, the composition operable to maintain approximately 75 to 100% of the hygroscopic compound concentration for a period of time, preferably at least 45 days, wherein the composition is soluble in water and the composition maintains its ability to readily flow when in a dry mode. In another embodiment, the composition can have more than one hygroscopic compound.

In another embodiment, the composition contains an inert carrier substrate having silica pores, a surface layer disposed on the outer surface of the inert carrier substrate, wherein the surface layer is permeable to oxygen and carbon dioxide, and a liquid additive loaded into the inert carrier substrate, wherein the average pore diameter of the liquid additive's molecules is less than the average diameter of the silica pores, and wherein the composition is operable to reduce contaminants from a contaminated area. In another embodiment, the liquid additive is bacteria, nutrients, or combinations thereof, the contaminated area is soil, water, or air, and the contaminants are sewage, oil, pollutants, or combinations thereof. In another embodiment, the composition is formed without the use of a chemical reaction. In another embodiment, the composition is formed without chemically altering the surface of the inert carrier substrate. In another embodiment, the composition is substantially dry such that it can readily flow. In one embodiment, the composition can exhibit an angle of repose between 29.9° and 42°. In one embodiment, the angle of repose can be determined by pouring the composition through a flannel and allowing the composition to fall onto a base board, thereby forming a conical mound. A portion of the base board can then be removed from underneath a portion of the conical mound. The angle formed by the edge of the board can be measured using a straight edge and reading the angle. In another embodiment, the composition has a Carr index value below 15. The Carr index is an indication of the compressibility of a powder. It is calculated by the formula:

$$C = 100 \frac{V_T - V_B}{V_T},$$

where $V_B$ is the freely settled volume of a given mass of powder, and $V_T$ is the tapped volume of the same mass of powder. The Carr index can also be expressed as:

$$C = 100 \times \left(1 - \frac{\rho_B}{\rho_t}\right),$$

where $\rho_B$ is the freely settled bulk density of the powder, and $\rho_T$ is the tapped bulk density of the powder. In another embodiment, the composition is not hygroscopic.

In another embodiment, the invention relates to the use of an inert carrier substrate as a delivery agent for the substance in a dry mode. In an embodiment, if the substance is in solid form, then the substance can be liquefied by melting or dissolving the substance in a carrier fluid, for example, water, alcohol, acetone, or the like. Once the substance is in a liquid state, the substance can be directly added to the inert carrier substrate in the presence of an organic phase, and mixed with the inert carrier substrate such that the substance infuses throughout the inert carrier substrate. A surface layer comprising the organic phase also forms on the outer surface of the inert carrier substrate to form a loaded product. In an additional embodiment, the organic phase can include an effective amount of oils, fatty acids, waxes, or combinations thereof. In one embodiment, the effective amount of fatty acids can include 2 to 15% by weight. In another embodiment, the effective amount of waxes can include 10 to 20% by weight. In another embodiment, the effective amount of oils can include 1 to 30% by weight. This loaded product can then be combined with other products or mixes and used in a wide range of products. Advantageously, substances which are hygroscopic, can be liquefied and loaded into inert carrier substrate, thereby allowing for handling in a dry mode. Additionally, different types of hygroscopic materials can be liquefied together to form a liquid blend that is well mixed to improve overall consistency. This liquid blend can be added to the inert carrier substrate, thereby allowing for the production of a loaded product that is highly consistent. Similarly, substances such as enzymes, bacteria, other microorganisms, nutrients, or combinations thereof, which are usually kept in a wet condition to maintain viability, can be loaded into the inert carrier substrate, thereby allowing for handling in a dry mode.

In another embodiment, an additional benefit is that the loaded product has an increased shelf life and/or can provide additional stability not accomplishable in a fluid state. For example, substances which are volatile, or substances which contain one or more hydroxyl groups. These unstable fluid substances often times can lose their efficacy after a few weeks, which means the end user must use the fluid substances quickly. In certain embodiments, these relatively unstable fluid substances can be loaded into precipitated silica to increase their shelf life and/or provide additional stability not accomplishable in a fluid state. As used herein, shelf life generally means the recommendation of time that products can be stored, during which the defined quality of a specified proportion of the goods remains acceptable under expected (or specified) conditions of distribution, storage and display. Some substances in their fluid states are relatively unstable.

In another embodiment, microbes, live cultures, and nutrients can be delivered in a dry format. In another embodiment, the delivery of these cultures and nutrients can be achieved by loading precipitated silica with the cultures, nutrients, and an organic phase, together or separately, to a desired capacity such that a surface layer forms on the outer surface of the inert carrier substrate, while the nutrients and cultures remain loaded throughout the pores of the inert carrier substrate. The loaded product can then be applied to the contamination on the water or in the soil. In another embodiment, the invention is applicable to spills, such as sewage, oil or other type of chemical contaminations on water since the loaded product adheres to the contaminate and keeps the cultures in direct contact with their food source, unlike liquid applications that may disperse without adhering to the contaminate. Embodiments of the present inventions can be also applicable to waste within landfills. Additional benefits can also be seen in microbe propagation (factors from ~1.5 to about 15 have been observed) and in the time release effects when the microbes are released over a period of time versus all at once as in a liquid application.

In another embodiment, a method for bioremediation can include loading inert carrier substrate with an emulsion to a desired capacity to form a loaded product, and applying the loaded product to an area having contaminants, such that the loaded product adheres to the contaminants and subsequently converts the contaminants into gaseous products and water thereby eliminating the contaminants from the area. In one embodiment, the emulsion can include an organic phase and a water phase, wherein the water phase can include water and microorganisms. In another embodiment, the water phase can further include nutrients, wherein the nutrients are water soluble. In another embodiment, the organic phase can include nonionic plant-based surfactants. In another embodiment, the organic phase can include fatty acid alcohols, fatty acids, lipids, and lecithin. In another embodiment, the organic phase can include lipids, fatty acids, and polysaccharides. In another embodiment, the area can be selected from the group consisting of water and soil. In another embodiment, the contaminants can be selected from the group consisting of sewage, oil, and combinations thereof. In one embodiment, the loaded product can by applied by the typical methods of aerial or manual broadcast spreading. For smaller spills, manual broadcast is preferred. For larger spills, particularly those in open water, marsh, wetlands, or estuary areas, aerial powder dusting or dusting with mechanical powder pumps is preferred. In one embodiment, approximately 0.4 pounds of the loaded product can be added per cubic yard of soil. In another embodiment, approximately 50 pounds of the loaded product can be added per acre of open water slick. In an embodiment wherein the area includes marsh, wetlands, or estuaries, up to 75 pounds of loaded product may be used per acre depending on the oil type and contamination level. In a preferred embodiment, the loaded product is applied directly on the contaminants.

Examples of liquid food additives include, without limitations, enzymes, bacteria, probiotics, oleoresin, flavors, minerals, plant extracts and preservatives. In one embodiment, the delivery of these ingredients can be achieved by loading precipitated silica, preferably food-grade, with the liquid ingredient(s), together or separately, to a desired capacity to form a loaded product. The loaded product can then be applied to a larger formulated recipe or packaged for later application or hydration. In other embodiments, the invention is applicable to concentrated ingredients such as extracts of all kinds, minerals, chelated minerals, vinegars, wine, soy sauce, pepper sauce, olive oil, essential oils, flavors and formulated liquid foods. Exemplary enzymes for liquid food additives include protease, amylase, cellulose, lipase, yeast.

Examples of liquid biotech agricultural ingredients include, without limitation, enzymes, bacteria, nutrients, wetting agents, and minerals. The delivery of these ingredients is achieved by loading precipitated silica with the liquid ingredient(s), together or separately, to a desired capacity then applying the loaded product to a larger formulated recipe or packaged for later application or hydration. In another embodiment, the invention is applicable to concentrated ingredients such as enzymes, bacteria nutrients and minerals. In one embodiment, liquid biotech agricultural ingredients are advantageous for treating "organic" produce or in the application and formulation of fertilizers, pesticides, herbicides, and the like.

Examples of conventional liquid agricultural ingredients include, without limitation, urea, potassium citrate, monopotassium phosphate, potassium chloride, magnesium chloride, sulfates, nutrients and minerals. The delivery of these ingredients is achieved by loading precipitated silica with the liquid ingredient(s), together or separately, to a desired capacity then applying the loaded product to a larger formulated recipe or packaged for later application or hydration. In another embodiment, the invention is applicable to concentrated ingredients such as, zinc, manganese, magnesium, boron, potassium, and phosphorus. In one embodiment, carbon, in either plant or non-plant based, can also be added to the composition. Advantageously, a pH value between 6.0 to 6.5 allows for improved propagation of any microbes or bacteria that may be in the loaded product. In another embodiment, the loaded product can be used in fresh or salt water applications having a pH of about 4 to about 11.5, and water temperatures of about 35° F. to about 170° F.

Examples of liquid human wellness and dietary supplements include, without limitation, essential oils and plant extracts, such as fish oil and other dietary items. The delivery of these ingredients is achieved by loading precipitated silica with the liquid ingredient(s), together or separately, to a desired capacity then applying the loaded product to a larger formulated recipe or packaged for later application or hydration. In another embodiment, the invention is applicable to concentrated ingredients such as, fish oils, amino acids, proteins and other supplements.

Examples of liquid media mixes for life sciences products include, without limitation, media mix elements such as blood media, soy media, sugar media, starch media and other similar media. In another embodiment, the delivery of these ingredients is achieved by loading precipitated silica with the liquid ingredient(s), together or separately, to a desired capacity then applying the loaded product to a larger formulated recipe or packaged for later application or hydration.

Examples of liquid fragrances and beauty products include, without limitation, essential oils and plant extracts, such as fragrances, amino acids, and glycolic acids. In another embodiment, the delivery of these ingredients is achieved by loading precipitated silica with the liquid ingredient(s), together or separately, to a desired capacity then applying the loaded product to a larger formulated recipe or packaged for later application or hydration. In another embodiment, the invention is applicable to concentrated ingredients such as fragrances, acids and oils.

Anther embodiment of the invention is a method for bioremediation. This method includes loading inert carrier substrate with a liquid substance to a desired capacity in the presence of an organic phase to form a loaded product having a surface layer, and applying the loaded product to an area having contaminants, such that the loaded product adheres to the contaminants and subsequently converts the contaminants into gaseous products and water thereby eliminating the contaminants from the area. In another embodiment, the liquid substance is microbes, nutrients, or combinations thereof. In another embodiment, the area is water or soil. In another embodiment, the contaminants are sewage, oil, or combinations thereof.

The present invention provides many benefits over conventional liquid additives including ease of use, lower shipping cost, ease of transportation, and reduced storage requirements.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION OF EMBODIMENTS OF THE PRESENT INVENTION

Embodiments of the present invention allow for the delivery of substances in a dry mode. In its most basic format, a predetermined amount of substance, if initially in liquid format, is added to an amount of an inert carrier substrate and mixed to form a loaded product having a semi-permeable surface layer. If the substance is initially in a dry format, the substance can be liquefied by various means known in the art and then added to an amount of the inert carrier substrate and mixed to form the loaded product. The loaded product has the consistency of a dry, sand-like substance. The loaded product includes the inert carrier substrate and the liquid substance loaded throughout the inert carrier substrate inner and outer surfaces, and a surface layer on the outer surface of the inert carrier substrate. In one embodiment, the surface layer is permeable to carbon dioxide and oxygen. Additionally, the surface layer includes an organic phase that can be made using a variety of techniques. The loaded product contains the characteristics of the substance, yet is dry to the touch. In one embodiment, the surface layer does not rub off or leave an oily feel to the skin.

In one embodiment of the invention, a composition for delivering microorganisms in a dry mode contains the inert carrier substrate having a porous structure, a surface layer permeable to carbon dioxide and oxygen, and microorganisms loaded throughout the pores of the inert carrier substrate. In another embodiment, the pores of the inert carrier substrate have diameters within the range of 38 to 240 nanometers. In another embodiment, the microorganisms are selected from the group consisting of bacteria, enzymes, fungi, archaea, viruses, algae, plankton, *planaria*, protists, and combinations thereof. In another embodiment, the composition can also include nutrients loaded throughout the pores of the inert carrier substrate. In another embodiment, the nutrients are selected from the group consisting of ammonia, nitrogen, ammonium nitrogen, urea, dextrose, dextrin, sugars, proteins, and combinations thereof. In another embodiment, the composition has an initial microorganism count, and the composition is operable to maintain approximately 75 to 400% of the initial cellular organism count for a period of time, preferably at least 45 days. In some embodiments, propagation levels have been observed at 30 to 100 times more than the original count within several days, and continued propagation well past 120 days. In one embodiment, the surface layer acts similarly to cell walls that can be found in bacteria (prokaryotes) and fungi (eukarotes), thereby supporting microbial life and propagation.

As noted previously, precipitated silica can be used in some embodiments of the present invention as the inert carrier substrate. The characteristics of typical precipitated silica are as follows: pore size range from 38-240 nanometers and a particle size of 10-1400 microns. Examples of precipitated silica useful as part of certain embodiments of compositions and methods of the present invention are the FLO-GARD® or HI-SIL® silicon dioxide products obtained from PPG Industries, Inc. Precipitated silica may also be obtained from other providers, such as for example, W. R. Grace and Company. Another characteristic of typical precipitated silica is a surface area of from about 140 to about 160 square meters per gram.

Examples of microorganisms to be used in this invention are bacteria, enzymes, fungi, archaea, viruses, algae, plankton, *planaria*, protists, or combinations thereof.

Examples of bacteria include without limitations: *bacillus*, prokaryotes and eukaryotes, gram positive and gram negative, *Actinobacteria, Firmicutes, Tenericutes, Aquificae, Bacteroidetes/Chlorobi, Chlamydiae/Verrucomicrobia, Deinococcus-Thermus, Fusobacteria, Gemmatimonadetes, Nitrospirae, Proteobacteria, Spirochaetes, Synergistetes, Acidobacteria, Chloroflexi, Chrysiogenetes, Cyanobacteria, Deferribacteres, Dictyoglomi, Fibrobacteres, Planctomycetes, Thermodesulfobacteria, Thermotogae, B. alvei, B. amyloliquefaciens, B. anthracis, B. cereus, B. circulans, B. coagulans, B. globigii, B. infernus, B. larvae, B. laterosporus, B. licheniformis, B. megaterium, B. mucilaginosus, B. natto, B. polymyxa, B. pseudoanthracis, B. pumilus, B. sphaericus, B. sporothermodurans, B. stearothermophilus, B. subtilis, B, thuringiensis*, or combinations thereof.

Examples of exemplary bacteria particularly useful for bioremediation applications include without limitations: pseudomonads, flavobacteriaceaes, and *bacillus, Pseudomonas fluorescence, Pseudomonas aeruginosa, Pseudomonas putida, Pseudomonas alcoligenes, Flavobacterim, Arthrobacter cumminsii, Alconivorax borkumensis, Vibrio parahaemolyticus*, or combinations thereof.

Examples of exemplary acid producing bacteria include without limitations: *Enterococcus faecium, Streptococcus faecium, Pediococcus acidilactici, Lactobacillus acidophilus, Lactobacillus plantarum*, or combinations thereof.

Enzymes are proteins that catalyze chemical reactions. Examples of enzymes include without limitations: acetolactatedecarboxylases, amylases, amyloglucosidases, anhydrases, arabinoxylanases, betaglucanases, carboxylases, catalases, cellulases, cyclases, dehydrogenases, dismuates, glucanases, glucoamylases, hydrolases, hydroxylases, isomerases, kinases, laccases, lactases, ligninases, luciferases, ligases, lipases, lyases, oxidases, oxidoreductrases, pectinases, phosphatases, proteases, pullulanases, reductases, rennin, transferases, transaminases, thiaminases, synthases, xylanases, DNA polymerases, DNA ligases, ceruloplasmin, restriction enzymes, papain, or combinations thereof.

Examples of fungi include without limitations: *Blastocladiomycota, Chytridiomycota, Glomeromycota, Microsporidia, Neocallimastigomycota, Dikarya, Deuteromycota, Ascomycota, Pezizomycotina, Saccharomycotina, Taphrinomycotina, Basidiomycota, Agaricomycotina, Pucciniomycotina, Ustilaginomycotina, Subphyla Incertae sedis, Entomophthoromycotina, Kickxellomycotina, Mucoromycotina, Zoopagomycotina*, or combinations thereof.

Examples of archaea include without limitations: *Crenarchaeota, Euryarchaeota, Korarchaeota, Nanoarchaeota, Thaumarchaeota*, or combinations thereof.

Examples of viruses include without limitations: dsDNA viruses: families: Myoviridae, Podoviridae, Siphoviridae, Alloherpesviridae, Herpesviridae, Malacoherpesviridae, Ascoviridae, Adenoviridae, Asfarviridae, Baculoviridae, Coccolithoviridae, Corticoviridae, Fuselloviridae, Guttaviridae, Iridoviridae, Lipothrixviridae, Nimaviridae, Papillomaviridae, Phycodnaviridae, Plasmaviridae, Polyomaviridae, Poxviridae, Rudiviridae, Tectiviridae, and Mimiviridae, and genera: *Ampullavirus, Nudivirus, Salterprovirus, Sputnik virophage*, and *Rhizidiovirus*; ssDNA viruses: families: Inoviridae, Microviridae, Geminiviridae, Circoviridae, Nanoviridae, and Parvoviridae, and genera *Anellovirus*; dsRNA viruses: families: Birnaviridae, Cystoviridae, Hypoviridae, Partitiviridae, Reoviridae, and Totiviridae, and genera *Endornavirus*; (+)ssRNA viruses: families: Arteriviridae, Coronaviridae, Roniviridae, Dicistroviridae, Iflaviridae, Marnaviridae, Piconaviridae, Secoviridae, Alphaflexiviridae, Betaflexiviridae, Gammaflexiviridae, Tymoviridae, Astroviridae, Barnaviridae, Bromoviridae, Caliciviridae, Closteroviridae, Flaviviridae, Leviviridae, Luteoviridae, Narnaviridae, Potyviridae, Tetraviridae, Togoviridae, and Tombusviridae, and genera: *Benyvirus, Furovirus, Hepevirus, Hordeivirus, Idaeovirus, Ourmiavirus, Pecluvirus, Pomovirus, Sobemovirus, Tobamovirus, Tobravirus*, and *Umbravirus*; (−)ssRNA viruses: families: Bornaviridae, Filoviridae, Paramyxoviridae, Rhabdoviridae, Arenaviridae, Bunyaviridae, and Orthomyxoviridae, and genera: *Deltavirus, Nyavirus, Ophiovirus, Tenuivirus*, and *Varicosavirus*; ssRNA-RT viruses: families: Metaviridae, Pseudoviridae, and Retroviridae; dsDNA-RT viruses: families: Hepadnaviridae and Caulimoviridae, or combinations thereof.

Examples of algae include without limitations: *Archaeplastida, Chlorophyta, Rhodophyta, Glaucophyta, Rhizaria, Excavata, Chlorarachniophytes, Euglenids, Chromista, Alveolate, Heterokonts, Bacillariophyceae, Axodine, Bolidomonas, Eustigmatophyceae, Phaeophyceae, Chrysophyceae, Raphidophyceae, Synurophyceae, Xanthophyceae, Cryptophyta, Dinoflagellates, Haptophyta*, or combinations thereof.

Examples of plankton include without limitations: phytoplankton, autotrophic, prokaryotic or eukaryotic algae, cyanobacteria, dinoflagellates and coccolithophores, zooplankton, small protozoans or metazoans, bacterioplankton, or combinations thereof. The equivalent spherical diameter of the plankton contemplated as part of this inventions is typically under 240 nanometers.

Examples of planaria include without limitations: *Dugesia tigrina, Planaria maculate, Dugesia dorotocephala, Schmidtea mediterranea*, or combinations thereof.

Examples of protists include without limitations: *Chromalveolata, Heterokontophyta, Haptophyta, Cryptophyta, Alveolata, Dinoflagellata, Apicomplexa, Ciliophora, Excavata, Euglenozoa, Percolozoa, Metamonada, Rhizaria, Radiolaria, Foraminifera, Cercozoa, Archaeplastida, Rhodophyta, Glaucophyta, Unikonta, Amoebozoa, Choanozoa*, or combinations thereof.

What follows is an example of how one can load microorganisms into precipitated silica granules. 700 ml of microorganisms *B. subtilis* in a fluid media with a count of 31 million cfu/g is introduced by evenly distributing fluids to 270 g of FLO-GARD SC72C precipitated silica granules using a stainless steel ribbon blender. Additionally, when a surface layer is desired, an organic phase can be added, either before, after, or at the same time as the other fluids. The subsequent mixture is stirred until all liquid media is substantially loaded into the precipitated silica granules. Nutrients can be blended with the microorganisms prior to being loaded with the precipitated silica granules or they may be loaded into separate precipitated silica granules stock so that the amount of nutrients in the precipitated silica granules is modified as needed. The temperature of the mixtures can be maintained at 10-40° C. The resulting product is dry to the touch within five minutes of the initial introduction of the liquid media. This dry state is reached during the stirring of the combined ingredients and is handled as a dry product immediately upon unloading the mixer. The product can be then stored at room temperature with an improved shelf life.

As used herein, the term "dry mode" means that a liquid is substantially loaded in the inert carrier substrate. One of ordinary skill in the art will understand that this is achieved during the mixing process when a liquid is loaded into the inert carrier substrate. In one embodiment, after mixing for five minutes, the resulting product is dry to the touch and can be handled as a dry product. Furthermore, the dry product is fully free flowing.

In another embodiment, a composition for delivering volatile fluids in a dry mode contains precipitated silica granules having a porous structure, a surface layer disposed on the outer surface of the inert carrier substrate, wherein the surface layer is permeable to oxygen and carbon dioxide, and volatile fluids loaded throughout the pores of the precipitated silica granules, the composition having 25 to 75% volatile fluid concentration by weight, the composition operable to maintain approximately 75 to 100% of volatile fluid concentration for a period of at least 45 days, wherein the volatile fluid has a vapor pressure of at least 0.03 atm at 25° Celsius. In another embodiment, a composition for delivering essential oils in a dry mode contains precipitated silica granules having a porous structure, a surface layer disposed on the outer surface of the inert carrier substrate, wherein the surface layer is permeable to oxygen and carbon dioxide, and an essential oil loaded throughout the pores of the precipitated silica granules, the composition having 25 to 75% essential oil concentration by weight, the composition operable to maintain approximately 75 to 100% of essential oil concentration for a period of at least 45 days.

In another embodiment, a composition for delivering a hygroscopic compound in a dry mode that maintains flow contains the inert carrier substrate having a porous structure, a surface layer disposed on the outer surface of the inert carrier substrate, wherein the surface layer is permeable to oxygen and carbon dioxide, and the hygroscopic compound loaded throughout the pores of the inert carrier substrate, the composition having 25 to 75% hygroscopic compound concentration by weight, the composition operable to maintain approximately 75 to 100% of the hygroscopic compound concentration for a period of at least 45 days, wherein the composition is soluble in water.

In another embodiment, a composition for delivering a liquid additive in a dry mode contains the inert carrier substrate having silica pores, a surface layer disposed on the outer surface of the inert carrier substrate, wherein the surface layer is permeable to oxygen and carbon dioxide, and a liquid additive loaded into the inert carrier substrate, wherein the average pore diameter of the liquid additive's molecules is less than the average diameter of the silica pores, wherein the composition is operable to reduce contaminants from a contaminated area. In another embodiment, the liquid additive is selected from the group consisting of bacteria, nutrients, and combinations thereof; the contaminated area is selected from the group consisting of soil, water, and air; and the contaminants are selected from the group consisting of sewage, oil, pollutants, and combinations thereof. In another embodiment, the composition is formed without the use of a chemical reaction. In another embodiment, the composition is formed without chemically altering the surface of the inert carrier substrate. In another embodiment, the composition is substantially dry such that it can readily flow. In another embodiment, the composition is not hygroscopic.

In another embodiment, the substances can be bacteria, enzymes, other microorganisms, or combinations thereof. In another embodiment, the substances are liquid additives that can be organic or inorganic, as defined by the USDA's National Organic Program, or combinations thereof. Exemplary liquid additives include liquid food, liquid food additives, liquid biotech agricultural ingredients, conventional liquid agricultural ingredients, liquid human wellness and dietary supplements, and liquid fragrances and beauty products.

In another embodiment, the invention relates to the use of the inert carrier substrate as a delivery agent for the substance in a dry mode. In an embodiment, if the substance is in solid form, then it can be liquefied by either melting or dissolving the substance in a carrier fluid, such as water, alcohol, glycerin, syrup, oil, acetone or other acceptable fluid media. Once the substance is in a liquid state, it can be added before, after, or with an organic phase, and mixed with the inert carrier substrate such that the substance infuses throughout the inert carrier substrate to form the loaded product having a surface layer. This loaded product can then be combined with other products or mixes and used in a wide range of products. Advantageously, substances that are hygroscopic can be liquefied and loaded into the inert carrier substrate, thereby allowing for handling in a dry mode (i.e., no clumping). Additionally, different types of hygroscopic materials can be liquefied together to form a liquid blend that is well mixed to improve overall consistency. This liquid blend can be added to the inert carrier substrate, thereby allowing for the production of a loaded product that is highly consistent. Similarly, substances such as enzymes, bacteria, other microorganisms, nutrients, or combinations thereof, which are usually kept in a wet condition to maintain viability, can be loaded into inert carrier substrate, thereby allowing for handling in a dry mode.

In another embodiment, an additional benefit is that the loaded product has an increased shelf life and/or provide additional stability not accomplishable in a fluid state. Some substances in their fluid states are relatively unstable. For example, substances which are volatile, or substances which contain one or more hydroxyl groups. These unstable fluid substances often times can lose their efficacy after a few weeks, which means the end user must use the fluid substances quickly. In certain embodiments, these relatively unstable fluid substances can be loaded into inert carrier substrate to increase their shelf life and/or provide additional stability not accomplishable in a liquid state.

In another embodiment, microbes, live cultures, and nutrients can be delivered in a dry format. In another embodiment, the delivery of these cultures and nutrients can be achieved by loading inert carrier substrate with the cultures and nutrients, together or separately, along with an organic phase, to a desired capacity then applying the loaded product to the contamination on the water or in the soil. In another embodiment, the invention can be applicable to spills, such as sewage, oil or other type of chemical contaminations on water since the loaded inert carrier substrate adheres to the contaminate and keeps the cultures in direct contact with their food source, unlike liquid applications that may disperse without adhering to the contaminate. Embodiments of the present invention can also be applicable to waste within landfills. Additional benefits can also be seen in microbe propagation (factors from ~1.5 to more than 15 have been observed) and in the time release effects when the microbes are released over a period of time versus all at once in a liquid.

Examples of liquid food additives include enzymes, bacteria, probiotics, oleoresin, flavors, minerals, plant extracts and preservatives. In one embodiment, the delivery, of these ingredients can be achieved by loading inert carrier substrate, preferably food-grade, with the liquid ingredient(s), together or separately, along with an organic phase, to a desired capacity to form the loaded product. The loaded product can then be applied to a larger formulated recipe or packaged for later application or hydration. In other embodiments, the invention can be applicable to concentrated ingredients such as extracts of all kinds, minerals, chelated minerals, vinegars, wine, soy sauce, pepper sauce, olive oil, essential oils, flavors and formulated liquid foods.

Examples of liquid biotech agricultural ingredients include enzymes, bacteria, nutrients and minerals. The delivery of these ingredients can be achieved by loading inert carrier substrate with the liquid ingredient(s), together or separately, along with an organic phase, to a desired capacity to form the loaded product having a surface layer. The loaded product can then be applied to a larger formulated recipe or packaged for later application or hydration. In another embodiment, the invention can be applicable to concentrated ingredients such as enzymes, bacteria, nutrients and minerals. In one embodiment, liquid biotech agricultural ingredients are advantageous for treating "organic" produce or in the application and formulation of fertilizers, pesticides, herbicides, etc.

Examples of conventional liquid agricultural ingredients include urea, potassium citrate, monopotassium phosphate, potassium chloride, magnesium chloride, sulfates, nutrients and minerals. The delivery of these ingredients can be achieved by loading inert carrier substrate with the liquid ingredient(s), together or separately, along with an organic phase, to a desired capacity to form the loaded product having a surface layer. The loaded product can then be applied to a larger formulated recipe or packaged for later application or hydration. In another embodiment, the invention can be applicable to concentrated ingredients such as, zinc, manganese, magnesium, boron, potassium, and phosphorus.

Examples of liquid human wellness and dietary supplements include essential oils and plant extracts, such as fish oil and other dietary items. The delivery of these ingredients can be achieved by loading inert carrier substrate with the liquid ingredient(s), together or separately, along with an organic phase, to a desired capacity to form the loaded product having a surface layer. The loaded product can then be applied to a larger formulated recipe or packaged for later application or hydration. In another embodiment, the invention can be applicable to concentrated ingredients such as, fish oils, amino acids, proteins and other supplements.

Examples of liquid media mixes for life sciences products include media mix elements such as blood media, soy media, sugar media, starch media and other similar media. In another embodiment, the delivery of these ingredients can be achieved by loading inert carrier substrate with the liquid ingredient(s), together or separately, along with an organic phase, to a desired capacity to form the loaded product having a surface layer. The loaded product can then be applied to a larger formulated recipe or packaged for later application or hydration.

Examples of liquid fragrances and beauty products include essential oils and plant extracts, such as fragrances, amino acids, and glycolic acids. In another embodiment, the delivery of these ingredients can be achieved by loading inert carrier substrate with the liquid ingredient(s), together or separately, along with an organic phase, to a desired capacity to form the loaded product having a surface layer. The loaded product can then be applied to a larger formulated recipe or packaged for later application or hydration. In another embodiment, the invention can be applicable to concentrated ingredients such as fragrances, acids and oils.

The present invention provides many benefits over conventional liquid additives including ease of use, lower shipping cost, ease of transportation, and reduced storage requirements.

In an embodiment wherein the substance can be a liquid food additive, the loaded product can be combined with other premixed spices that are found with ready to make soups, gravies, sauces, dips, etc. The loaded product could also be sold in individual packages much like sweeteners or tea bags. In this fashion, liquid food additives could be easily packaged for travel sizes in a dry form. The dry, loaded product provides many benefits over its liquid food additive counterparts. For example, the loaded product increases overall ease of use, eliminates spoilage, increases food preservation and food safety, lowers shipping costs, increases ease of transportation, and reduces storage requirements. Another advantage is that the loaded product does not require the need for cold storage, which eliminates the need for refrigeration when the user is at home or on the go.

Many different liquid food products are encompassed within embodiments of the present invention. Extracts of all kinds, minerals, chelated minerals, vinegars, wine, soy sauce, pepper sauce, alcohol, Worcester Sauces, olive oil, and essential oils are all encompassed by the present invention. Of course, those of ordinary skill in the art will recognize other equivalents as well.

EXPERIMENTAL RESULTS

Sample 1—Preparation of the Precipitated Silica Granules Loaded with B. Subtilis (No Surface Layer)

700 ml of microorganisms B. subtilis in a liquid media with a count of 31 million cfu/g was introduced through a fine mist spray technology, that evenly distributes liquids over dry substances, using a stainless steel ribbon blender to 270 g of FLO-GARD SC72C precipitated silica granules. The subsequent mixture was stirred until all liquid media is substantially loaded into the precipitated silica granules. Nutrients were blended with the microorganisms prior to being loaded with the precipitated silica; however, they may be loaded into separate precipitated silica stock so that amount of nutrients in the precipitated silica granule can be modified as needed. The temperature of the mixtures can be maintained at 10-40° C. The resulting product was dry to the touch within five minutes of the initial introduction of the liquid media. This dry state was reached during the stirring of the combined ingredients and was handled as a dry product immediately upon unloading the mixer. The product can be then stored at room temperature. The activity of microorganisms contained in the precipitated silica granules were measured.

The way the activity of a microorganism can be measured depends on the microorganism. For example, for B. subtilis, a method to measure its activity was as follows. An 11 gram sample was diluted and plated serially from 100 to 1,000,000. A 0.1 mL portion of each dilution was then placed onto an MYP agar plate and spread on the surface. It was then incubated for 72 hours at 30° C. Suspect colonies were then confirmed and reported as the confirmed colonies CFU/g (see FDA Bacterialog. Analytical Manual, 8th Ed. Ch.14 (this method was originally developed to measure B. cereus but was modified according to the Gorton Industries Protocol to measure B. subtilis)). Table I below describes the results of those measurements.

TABLE I

Bacillus Counts Over Time

| Days After Preparation | Bacillus Count (xMM) |
|---|---|
| 1 | 200 |
| 10 | 210 |
| 20 | 310 |
| 30 | 230 |

Sample 2—Preparation of Nutrients Loaded Precipitated Silica Granules (No Surface Layer)

A 55:1 dilution of Tri-Phasic-12™ was prepared. Tri-Phasic-12™ was obtained from Micro-Bac International, Inc., 3200 N. IH-35, Round Rock, Tex. 78681-2410. The diluted solution had a ratio of 1:55 nutrients to water. 522.1 ml of diluted nutrients was added to 206.8 g of precipitated silica granules into a stainless steel blender, yielding a loaded product that is 72% loaded.

Sample 3—Preparation of the Precipitated Silica Granules Loaded with B. Subtilis and Having a Surface Layer A first solution was created by solubilizing 10 g of cetearyl alcohol and 10 g of cetyl ester at 165° F. and using a slow speed mechanical blender. A second solution was created by mixing together 0.5 g lecithin, 5 g olive oil, and 5 g canola oil. A third solution was created by mixing 1.5 ml of B. Subtilis with 70.5 ml of distilled water. The first two solutions were combined and mixed together. The third solution was then subsequently added to form an emulsion having an organic phase and a water phase. While this embodiment combined the three solutions in this manner, it should be understood that they may be combined in other orders. Preferably, the solutions are combined at a temperature lower than the temperature at which the bacteria are destroyed. In some embodiments, this top temperature is approximately 110° F.: Therefore, a preferred mixing temperature can be in the range of 80° F. to 90° F. Following the mixing step, there is an optional cooling step to room temperature. The emulsion is typically in a pasty, creamy emulsion when cooled to room temperature.

The emulsion was then added to the precipitated silica granules using a mixing/blending system. A slow mixing speed is preferred. After about 5 minutes, the loaded product having a surface layer is formed. In the present embodiment, the surface layer is comprised of fatty acid alcohols, fatty acids, and lipids, while the water and B. Subtilis are located within the precipitated silica granules.

Sample 4—Preparation of the Precipitated Silica Granules Loaded with B. Subtilis and Having a Surface Layer A first solution was created by solubilizing 85 g of cetearyl alcohol and 85 g of cetyl ester at 165° F. and using a slow speed mechanical blender. A second solution was created by mixing together 8 g lecithin, 84 g olive oil, and 40 g canola oil. A third solution was created by mixing 2.4 ml of B. Subtilis with 115.6 ml of distilled water. The first two solutions were combined and mixed together. The third solution was then subsequently added to form an emulsion having an organic phase and a water phase. While this embodiment combined the three solutions in this manner, it should be understood that they may be combined in other orders. Preferably, the solutions are combined at a temperature lower than the temperature at which the bacteria are destroyed. In some embodiments, this top temperature is approximately 110° F. Therefore, a preferred mixing temperature can be in the range of 80° F. to 90° F. Following the mixing step, there is an optional cooling step to room temperature. The emulsion is typically in a pasty, creamy emulsion when cooled to room temperature.

The emulsion was then added to the precipitated silica granules using a mixing/blending system. A slow mixing speed is preferred. After about 5 minutes, the loaded product having a surface layer is formed. In the present embodiment, the surface layer is comprised of fatty acid alcohols, fatty acids, and lipids, while the water and B. Subtilis are located within the precipitated silica granules.

Sample 5—Preparation of the Precipitated Silica Granules Loaded with B. Subtilis and Having a Surface Layer A first solution was created by solubilizing 63 g of cetearyl alcohol and 63 g of cetyl ester at 165° F. and using a slow speed mechanical blender. A second solution was created by mixing together 11 g lecithin, 126 g olive oil, and 0 g canola oil. A third solution was created by mixing 3.1 ml of B. Subtilis with 153.9 ml of distilled water. The first two solutions were combined and mixed together. The third solution was then subsequently added to form an emulsion having an organic phase and a water phase. While this embodiment combined the three solutions in this manner, it should be understood that they may be combined in other orders. Preferably, the solutions are combined at a temperature lower than the temperature at which the bacteria are destroyed. In some embodiments, this top temperature is approximately 110° F. Therefore, a preferred mixing temperature can be in the range of 80° F. to 90° F. Following the mixing step, there is an optional cooling step to room temperature. The emulsion is typically in a pasty, creamy emulsion when cooled to room temperature.

The emulsion was then added to the precipitated silica granules using a mixing/blending system. A slow mixing speed is preferred. After about 5 minutes, the loaded product having a surface layer is formed. In the present embodiment, the surface layer is comprised of fatty acid alcohols, fatty acids, and lipids, while the water and *B. Subtilis* are located within the precipitated silica granules.

In another embodiment, the composition can be created by combining a wax, cetearyl alcohol, a fatty acid, an emulsifier, water, and microorganisms with an inert carrier substrate. In one embodiment, the wax can include bees wax. Other exemplary waxes include candelilla wax, jojoba wax, and carnauba wax. In another embodiment, the fatty acids can include olive oil, canola oil, sunflower oil, vegetable oil, or combinations thereof. In another embodiment, the emulsifier can be lecithin. In one embodiment, the wax can be present in an amount from 1% to 40%, more preferably 10% by weight. In one embodiment, the cetearyl alcohol can be present in an amount from 1% to 15%, more preferably 2% by weight. In one embodiment, the fatty acids can be present in an amount from 2% to 40%, more preferably 15% by weight. In one embodiment, the emulsifier can be present in an amount from 1% to 7%, more preferably 3% by weight. In one embodiment, the water/microorganism solution can be present in an amount from 1% to 50%, more preferably 2-3% by weight. In one embodiment, the water/microorganism solution contains 70% to 99% water, more preferably 97% water, and 1% to 30% microorganisms, more preferably 3% microorganisms by volume.

In another embodiment, the composition can be created by combining a wax, cetearyl alcohol and/or cetyl ester, a fatty acid, an emulsifier, water, and microorganisms with an inert carrier substrate. In one embodiment, the wax can include bees wax. In another embodiment, the fatty acids can include olive oil, canola oil, sunflower oil, vegetable oil, or combinations thereof. In another embodiment, the emulsifier can be lecithin. In one embodiment, the wax can be present in an amount from 1% to 40%, more preferably 10% by weight. In one embodiment, the cetearyl alcohol can be present in an amount from 1% to 15%, more preferably 2% by weight. In one embodiment, the cetyl ester can be present in an amount from 1% to 15%, more preferably 2% by weight. In one embodiment, the fatty acids can be present in an amount from 2% to 40% more preferably 15% by weight. In one embodiment, the emulsifier can be present in an amount from 1% to 7%, more preferably 3% by weight. In one embodiment, the water/microorganism solution can be present in an amount from 1% to 50%, more preferably 2-3% by weight. In one embodiment, the water/microorganism solution contains 70% to 99% water, more preferably 97% water, and 1% to 30% microorganisms, more preferably 3% microorganisms by volume.

In one embodiment, the water/microorganism solution can contain 98% water and 2% microorganisms by volume.

In another embodiment, the water/microorganism solution can contain between 95% to 98% water and 2% to 5% microorganisms as measured by volume.

Table II to Table IV below provides a summary of examples of formulas to create the emulsion that, when mixed sufficiently with an effective amount of precipitated silica, were operable to create a loaded product having a surface layer. Percentages are by weight of the emulsion prior to mixing with the precipitated silica. The fatty acid oils were selected from the group of olive oil, canola oil, sunflower oil, vegetable oil, and combinations thereof. The wax was selected from the group of candelilla wax, bee's wax, jojoba wax, and combinations thereof.

TABLE II

Composition of Formula 1

| Ingredient | Lower End (PBW) | Upper End (PBW) |
|---|---|---|
| water | 50 | 72 |
| microbes | 1 | 8 |
| emulsifier (lethecin) | 1 | 7 |
| fatty acid alcohol (cetearyl alcohol) | 1 | 15 |
| fatty acid oils | 2 | 40 |
| cetyl ester | 2 | 15 |

TABLE III

Composition of Formula 2

| Ingredient | Lower End (PBW) | Upper End (PBW) |
|---|---|---|
| water | 50 | 72 |
| microbes | 1 | 8 |
| emulsifier (lethecin) | 1 | 7 |
| fatty acid alcohol (cetearyl alcohol) | 1 | 15 |
| fatty acid oils | 2 | 40 |
| wax | 1 | 40 |

TABLE IV

Composition of Formula 3

| Ingredient | Lower End (PBW) | Upper End (PBW) |
|---|---|---|
| water | 50 | 72 |
| microbes | 1 | 8 |
| emulsifier (lethecin) | 1 | 7 |
| fatty acid alcohol (cetearyl alcohol) | 1 | 15 |
| fatty acid oils | 2 | 40 |
| cetyl ester | 2 | 15 |
| wax | 1 | 40 |

Those of ordinary skill in the art will recognize that the examples noted above are merely exemplary.

Figure 1:
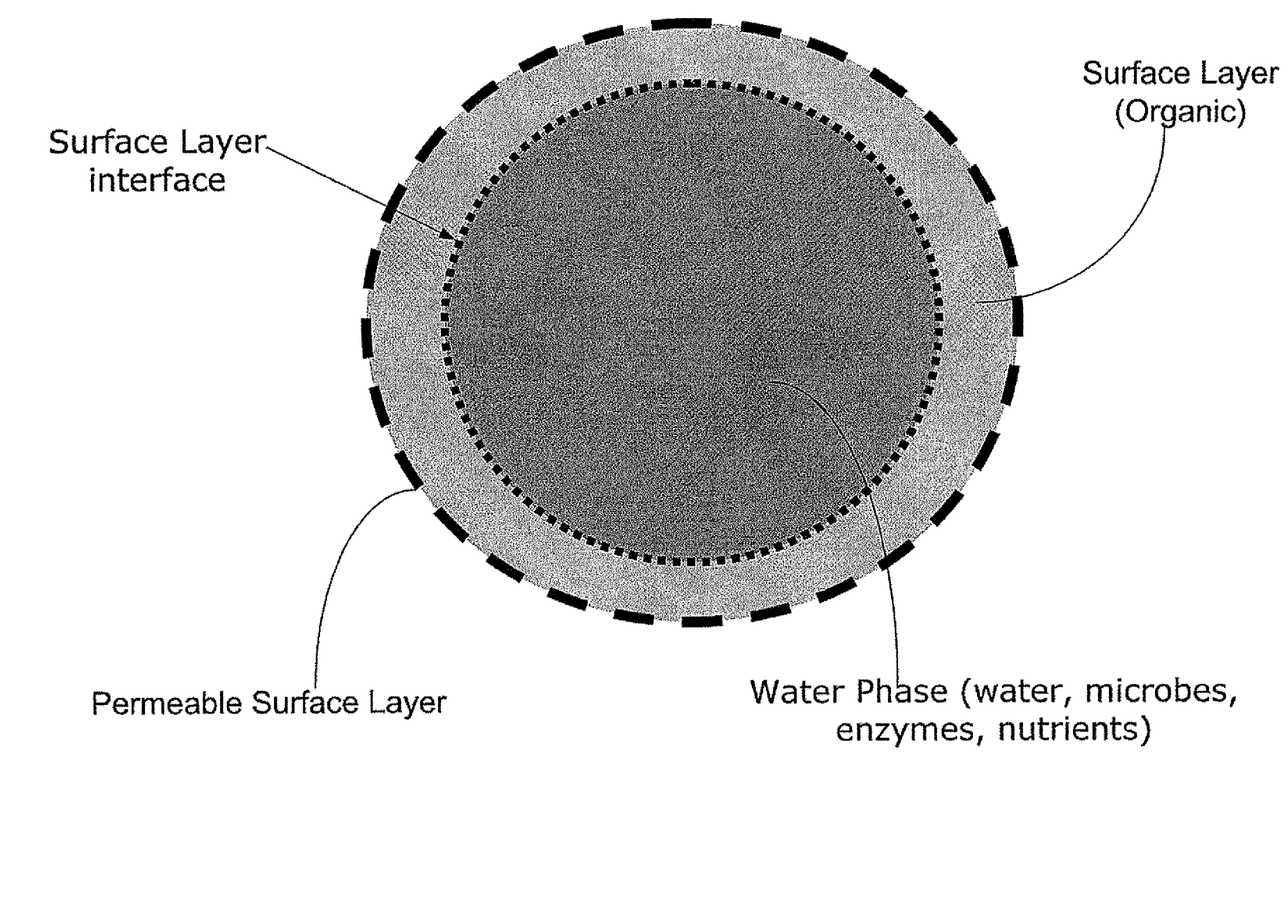
FIG. 1 is a cross sectional diagram of a composition in accordance with an embodiment of the present invention.

FIG. 1 represents a cross sectional view of a loaded product having a surface layer that is loaded with water, microbes, enzymes, and nutrients. As shown in FIG. 1, the water phase is located within the pores of the inert carrier substrate and is essentially trapped inside the surface layer. A surface layer interface can be formed between the surface layer and the water phase. The dashed lines of the surface layer interface and the surface layer are representative of the advantageous permeability of the surface layer, which allows for oxygen and carbon dioxide to move in and out of the loaded product. This keeps the water phase within the loaded product while also allowing for the microbes and enzymes to "breathe," which aids in propagation. Additionally, the surface layer keeps the replication controlled and contained within the surface layer interface.

Performance Tests Using a Composition in Accordance with an Embodiment of the Present Invention for Bioremediation A total of five samples of oil were prepared using 500 mg of oil. Three were considered control groups and the other two were used to test a composition in accordance with an embodiment of the present invention, (the "loaded product"). At day 0, the control group had an average about 41,277 ng/mg of alkanes and 6,100 ng/mg of aromatics. At day 28, the control group have an average of about 42,451 ng/mg of alkanes and 4,546 ng/mg of aromatics. At day 0 for the loaded product test group, there was 40,239 ng/mg alkanes and 5,814 ng/mg aromatics. At day 28 for the loaded product test group, the alkanes and aromatics concentration decreased dramatically to 155 ng/mg and 444 ng/mg, respectively. This is a reduction of approximately 99.6% and 92.4% in the alkane and aromatic concentrations, respectively. A summary of the results can be found in Table V below:

TABLE V

Performance Tests for Loaded Product

| Day | Controlled | | Loaded Product | |
|---|---|---|---|---|
| | Alkanes | Aromatics | Alkanes | Aromatics |
| 0 | 41277 | 6100 | 40239 | 5814 |
| 28 | 42451 | 4546 | 155 | 444 |
| % Reduction | N/A | N/A | 99.61% | 92.36% |

Table VI below shows comparative bioremediation results for products currently on the market. The results were taken from the EPA's website at www.epa.gov/OEM/content/ncp/tox_tables.htm (last accessed on Nov. 12, 2010). When comparing the loaded product with the best performing product below, it becomes clear that the loaded product, which is a composition in accordance with an embodiment of the present invention, outperforms everything on the market, particularly in aromatic reduction.

TABLE VI

Comparative Bioremediation Results

| | Effectiveness (28 day) | |
|---|---|---|
| Product | Alkanes (reduction %) | Aromatics (reduction %) |
| SYSTEM E.T. 20 | 99.1 | 77 |
| BET BIOPETRO | 99 | 67 |
| BILGE CLEAR (see S-200) | 98 | 10.4 |
| S-200 | 98 | 10.4 |
| S-200C (see S-200) | 98 | 10.4 |
| SHEENCLEAN (see S-200) | 98 | 10.4 |
| BIOWORLD BIOREMEDIATION TREATMENT PRODUCTS | 97 | 88 |
| SPILLREMED (MARINE) ® | 97 | 47 |
| *VB591 ™, VB997 ™, BIONUTRIX ® | 96.8 | 73.1 |
| MICRO-BLAZE ® | 94.1 | 47.6 |
| INIPOL EAP 22 (no longer manuf.) | 93.87 | 23.25 |
| JE1058BS | 92.6 | 39 |
| OIL SPILL EATER II (OSE II) | 89.8 | 89.6 |
| GENISIS WE-F (see OPPENHEIMER FORMULA) | 89.1 | 38.2 |
| MIGHTY MIKE BPT (see OPPENHEIMER FORMULA) | 89.1 | 38.2 |

TABLE VI-continued

Comparative Bioremediation Results

| | Effectiveness (28 day) | |
|---|---|---|
| Product | Alkanes (reduction %) | Aromatics (reduction %) |
| MUNOX SR ® | 94.9 | 75.5 |
| NATURAL ENVIRO 8000 BIOREMEDIATION (see OPPENHEIMER FORMULA) | 89.1 | 38.2 |
| OPPENHEIMER FORMULA | 89.1 | 38.2 |
| PETRO-TREAT (see OPPENHEIMER FORMULA) | 89.1 | 38.2 |
| PRISTINE SEA II (no longer manuf.) | NA | NA |
| WMI-2000 | 60.3 | 33.3 |
| B&S INDUSTRIAL (see STEP ONE) | 44.03 | 54.51 |
| STEP ONE | 44.03 | 54.51 |
| LAND AND SEA RESTORATION PRODUCT 001 (VELITE) | 42.92 | 31.92 |

Improved Microbe Propagation

An experiment was conducted to determine the advantage the surface layer can provide for microbe propagation. In this experiment, precipitated silica loaded with microbes and not having a surface area was prepared using 20 ml of liquid microbes and 8.57 g of precipitated silica. A second batch, made in accordance with an embodiment of the present invention, was prepared using 20 ml of polysorbate 80, 20 ml polyethylene glycol 400, 20 ml of liquid microbes, 38 ml of medium-chain triglycerides, 2 ml whey protein concentrate 80, and 42.86 precipitated silica. A lactic acid bacteria plate count, in accordance with CMMEF, $4^{th}$ ed., Method 19.5, was conducted on the two samples. The initial count of the liquid microbes was 230 million. The loaded product without a surface layer increased to 440 million, whereas the loaded product with surface layer increased to 1.9 billion. As such, the loaded product with surface layer made in accordance with an embodiment of the present invention achieved more than a 330% increase in microbe propagation as compared to the loaded silica without the surface layer.

Those skilled in the art will recognize that many changes and modifications can be made to the method of practicing the invention without departing the scope and spirit of the invention. In the drawings and specification, there have been disclosed embodiments of the invention and, although specific terms are employed, they are used in a generic and descriptive sense only and not for the purpose of limitation, the scope of the invention being set forth in the following claims. The invention has been described in considerable detail with specific reference to these illustrated embodiments. It will be apparent, however, that various modifications and changes can be made within the spirit and scope of the invention as described in the foregoing specification. Furthermore, language referring to order, such as first and second, should be understood in an exemplary sense and not in a limiting sense. For example, it can be recognized by those skilled in the art that certain steps can be combined into a single step.

The present invention may suitably comprise, consist or consist essentially of the elements disclosed and may be practiced in the absence of an element not disclosed. Furthermore, language referring to order, such as first and second, should be understood in an exemplary sense and not in a limiting sense. For example, it can be recognized by those skilled in the art that certain steps can be combined into a single step.

The singular forms "a", "an" and "the" include plural referents, unless the context clearly dictates otherwise. By way of example, the term "a food additive" could include one or more food additives used for the stated purpose.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these reference contradict the statements made herein.

What is claimed is:

1. A composition for delivering microorganisms in a dry mode, the composition comprising:

an inert carrier substrate comprising a plurality of particles, wherein an individual particle of the plurality of particles has a porous structure, wherein the inert carrier substrate is selected from the group consisting of diatomaceous earth, walnut and pecan shells, rice hulls, cellulosic clay, montmorillonite clay, bentonite clay, wool, cotton, cellulose, corn cobs, cellulose shells, precipitated silica, and combinations thereof;

a water phase comprising microorganisms, wherein the water phase and microorganisms are loaded throughout the porous structure of the individual particle; and a surface layer disposed on the outer surface of and encapsulating the individual particle and water phase comprising microorganisms, wherein the surface layer includes an organic phase and is permeable to molecules that aid in cell growth of the microorganisms such that the composition is operable to allow for propagation of the microorganisms within the porous structure of the individual particle, and wherein the propagation is increased as compared to another individual particle having an absence of the surface layer.

2. The composition as defined in claim 1, wherein the molecules that permeate the surface layer include oxygen and carbon dioxide.

3. The composition as defined in claim 1, wherein the surface layer is operable to allow for oxygen exchange, nutrient exchange, respiration, carbon dioxide production and digestion, and enzyme production.

4. The composition as defined in claim 1, wherein the inert carrier substrate is precipitated silica.

5. The composition as defined in claim 1, wherein the composition has a shelf life of at least two years.

6. The composition as defined in claim 1, wherein the surface layer consists of an organic phase.

7. The composition as defined in claim 6, wherein the organic phase is selected from the group consisting of fatty acid alcohols, fatty acids, lipids, lecithin, polysaccharides, and combinations thereof.

8. The composition as defined in claim 6, wherein the organic phase comprises fatty acids, lipids, and lecithin.

9. The composition as defined in claim 8, wherein the fatty acid is selected from the group consisting of saturated fatty acids, unsaturated fatty acids, and combinations thereof.

10. The composition as defined in claim 8, wherein the fatty acid is selected from the group consisting of palmitic acid, steric acid, arachidic acid, behenic acid, myristic acid, lignoceric acid, oleic acid, palmitoleic acid, linoleic acid, linolenic acid, Omega-3, Omega-6, and combinations thereof.

11. The composition as defined in claim 8, wherein the fatty acid is derived from a source selected from the group consisting of coconut oils, palm oils, vegetable oils, fish oils, and combinations thereof.

12. The composition as defined in claim 6, wherein the organic phase comprises nonionic plant-based surfactants.

13. The composition as defined in claim 6, wherein the organic phase comprises fatty acid alcohols, fatty acids, lipids, and lecithin.

14. The composition as defined in claim 6, wherein the organic phase comprises an emulsifier.

15. The composition as defined in claim 6, wherein the organic phase is comprised of lipids, fatty acids, and polysaccharides.

16. The composition as defined in claim 6, wherein the organic phase is formed when an emulsion is mixed with the inert carrier substrate, the emulsion is formed by mixing a combination of ingredients, wherein the ingredients are selected from the group consisting of lipids, polysaccharides, fatty acids, lecithin, plant-based surfactants, emulsifiers, and combinations thereof.

17. The composition as defined in claim 1, wherein the surface layer is substantially impermeable to fresh water.

18. The composition as defined in claim 1, wherein the surface layer is substantially impermeable to deionized water.

19. The composition as defined in claim 1, wherein the surface layer can be permeated by surfactants, oil, organic solvents, salt water, damp soil, or combinations thereof.

20. The composition as defined in claim 1, wherein the surface layer is at least partially soluble to surfactants, oil, organic solvents, salt water, damp soil, or combinations thereof.

21. The composition as defined in claim 1, wherein the surface layer further comprises an absence of a protein.

22. The composition as defined in claim 1, further comprising an absence of zeolites.

23. The composition as defined in claim 1, further comprising an absence of aluminosilicates.

24. The composition as defined in claim 1, further comprising an absence of a mineral powder.

25. The composition as defined in claim 1, wherein the composition is operable to breakdown hydrocarbon deposits in water or soil when introduced to water or soil.

26. The composition as defined in claim 1, wherein the composition is operable to breakdown hydrocarbon deposits in water or soil while the composition is in a dry state.

27. The composition as defined in claim 1, further comprising an absence of an acidic polymer.

28. The composition as defined in claim 1, further comprising nutrients in contact with the microorganisms, wherein the nutrients are operable to provide a food source to the microorganisms loaded throughout the porous structure of the inert carrier substrate such that the microorganisms can propagate.

29. The composition as defined in claim 28, wherein the nutrients are selected from the group consisting of ammonia, nitrogen, ammonium nitrogen, urea, dextrose, dextrin, sugars, proteins, and combinations thereof.

30. The composition as defined in claim 1, wherein pores of the porous structure have diameters within the range of 38 to 240 nanometers.

31. The composition as defined in claim 1, wherein the microorganisms are selected from the group consisting of bacteria, fungi, archaea, viruses, algae, plankton, *planaria*, protists, and combinations thereof.

32. The composition as defined in claim 31, wherein the microorganisms are bacilli.

33. The composition as defined in claim 1, wherein the composition has an initial microorganism count, and the composition is operable to maintain approximately 50 to 400% of the initial microorganism count for at least 45 days.

34. A composition for delivering microorganisms in a dry mode, the composition comprising:
   an inert carrier substrate comprising a plurality of particles, wherein an individual particle of the plurality of particles has a porous structure, and wherein the inert carrier substrate is precipitated silica;
   a water phase comprising microorganisms, wherein the water phase and the microorganisms are loaded throughout the porous structure of the individual particle; and
   a surface layer disposed on the outer surface of and encapsulating the individual particle and water phase comprising microorganisms, wherein the surface layer is permeable to molecules that aid in cell growth of the microorganisms such that the composition is operable to allow for propagation of the microorganisms within the porous structure of the individual particle, and wherein the propagation is increased as compared to another individual particle having an absence of the surface layer.

* * * * *